United States Patent [19]

Helbig

[11] 4,192,865

[45] Mar. 11, 1980

[54] SEDATIVE PREPARATION FOR ANIMALS AND METHOD

[75] Inventor: Joachim Helbig, Tutzing, Fed. Rep. of Germany

[73] Assignee: Verlapharm von Ehrlich A.G., Emmenbrücke, Switzerland

[21] Appl. No.: 900,568

[22] Filed: Apr. 27, 1978

[30] Foreign Application Priority Data

May 5, 1977 [DE] Fed. Rep. of Germany ....... 2720288

[51] Int. Cl.$^2$ .................... A61K 33/14; A61K 31/195
[52] U.S. Cl. .................................. 424/153; 424/154; 424/319
[58] Field of Search ........................ 424/154, 153, 319

[56] References Cited

PUBLICATIONS

Helbig et al.—Chem. Abst., vol. 85 (1976), pp. 182, 413x.
Hamanaka—Chem. Abst., vol. 83 (1975), p. 37574e.
Ebel et al.—Chem. Abst., vol. 83 (1975), pp. 126, 366f.
Fischer et al.—Chem. Abst., vol. 80 (1974), p. 96355.

*Primary Examiner*—Sam Rosen
*Attorney, Agent, or Firm*—Browdy and Neimark

[57] ABSTRACT

The invention concerns sedative preparations suitable for calming of animals and a method of sedating a warm-blooded animal other than human, comprising the step of administering to such a warm-blooded animal which it is desired to sedate, a magnesium aminodicarboxylic acid chloride, or a magnesium salt of an aminodicarboxylic acid in combination with magnesium chloride, at a dosage sufficient to sedate said warm-blooded animal.

9 Claims, No Drawings

SEDATIVE PREPARATION FOR ANIMALS AND METHOD

This invention relates to a method of sedating warm-blooded animals such as pigs, cattle and horses. Difficult problems arise because of the sensitivity of animals to stress situations. For example, dependent on such factors as breed, transporting conditions, weather and the like up to 5% pigs die during transport to slaughter houses because of their excitability. Losses can be even greater when the distances which animals need to be transported are great and which require several days or weeks, for example with transport of horses, cattle, sheep and pigs which are in these times transported over great distances by sea or air. Similar observations can also be made with chickens and also birds, for example exotic birds which are sometimes also transported over long distances to where they will be kept. States of exitement and aggressiveness associated therewith is probably also the reason for cannibalism in pigs which are kept in stalls. Larger animals, such as horses and cattle can cause significant problems because of their excitability not only when transported but also when being handled such as when being weighed.

For the above reasons, treatment of excitable animals, particularly horses, cattle and pigs, to calm states of excitement in stress situations, has been carried out with sedatives and psychopharmacological drugs. Such substances are amongst others based on Acepromazine or Azaperone (4'-fluoro-4-[4-(2-pyridyl)-1-pyperazinyl]-butyrophenone). These substances however have the disadvantage that they mostly need to be injected and also that they for example build up residuals of the substance itself or degeneration products thereof in the liver and partly also in the kidneys. Thus, particularly with intake of these organs by humans, considerable residual problems can arise; it can be expected that the activity in humans of the substances is similar to activity in slaughter animals and negative side effects can not be excluded. Other than possible allergic reactions, alcohol and other drugs which may be consumed by humans could lead to a potentiation of activity.

It is therefore an object of the invention to provide a physiological acceptable sedative substance which is well resorbed and can therefore be employed in low amounts, and which does not lead to build up in the liver of the substance or degeneration products thereof. In accordance with the invention, a preparation for treating of warm-blooded animals, particularly horses, cattle, pigs, sheep or poultry, is provided which is characterised in that it comprises a magnesium aminodicarboxylic acid chloride, or a magnesium salt of an aminodicarboxylic acid in combination with magnesium chloride. More particularly, the preparation is provided for sedating a warm-blooded animal other than human. The invention also concerns a method of sedating a warm-blooded animal other than human, which comprises the step of administering to such a warm-blooded animal which it is desired to sedate, a magnesium aminodicarboxylic acid chloride, or a magnesium salt of an aminodicarboxylic acid in combination with magnesium chloride, at a dosage sufficient to sedate said warm-blooded animal.

The magnesium aminodicarboxylic acid chloride is preferably magnesium glutamate hydrochloride or magnesium aspartate hydrochloride and the magnesium salt of the aminodicarboxylic acid is preferably magnesium diglutamate or magnesium diaspartate.

In German Pat. No. 1 809 119 there is described an infarct prophylactic preparation for use in human medicine, in which the active agent is magnesium aspartate chloride (or hydrochloride) of the formula:

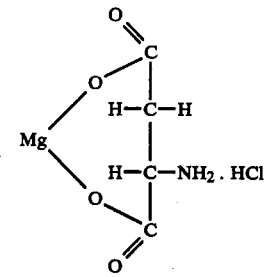

The above compound, and also the corresponding magnesium glutamate chloride, is well resorbed and may be employed in the preparation and method of the present invention either alone or in combination with magnesium glutamate chloride.

The fact that magnesium aspartate chloride does not lead to sedation in humans even at high doses, although plasma magnesium levels are significantly increased (compare H. Ebel, H.-G. Classen, P. Marquardt and M. Spath "Zur Pharmakologie und Pharmakokinetik von Magnesium", Munch. med. Wschr. 117, 29/30 (1975), 1243–1248, particularly FIG. 4) does not suggest that such compounds can be employed as sedatives in warm-blooded animals. Furthermore, it is known from test animal experimentation that magnesium aspartate chloride, magnesium chloride and magnesium diaspartate do not lead to any sedative action in rats also at extremely high doses of 500 mg/kg animal body weight, in spite of the compounds being well resorbed in rats and a significant increase in plasma magnesium levels (compare H. G. Classen, P. Marquardt, M. Späth, H. Ebel, K.-A. Schumacher, J. Helbig and B. Gräbling, "Magensium Concentrations and Combinations", Arzeimittel-Forschung (Drg.Res. 26, 2 (1976) 249 to 253, particularly Table I).

It is therefore all the more surprising that an effective sedation of larger animals such as horses, cattle, pigs or sheep, and also poultry, can be determined when plasma magnesium levels are raised in these animals by administration of the magnesium compounds employed in the present invention. By virtue of this sedative action, it is noteworthy that an improvement in quality of meat can be expected in cattle and pigs which have been treated in accordance with the invention over a period of time.

The plasma magnesium levels in pigs following on administration of magnesium aspartate chloride (Mg Asp HCl) in a feed additive mixture can be seen from the following Table I.

Table I

Mean values of two double determinations in double-blind experiments as compared to a controll group, interpolated on the initial value (=0) before feeding.

| | Time of Determination | | | |
|---|---|---|---|---|
| | 1st day | 2nd day | 3rd day | 4th day |
| | before feeding of feed additive mixture | after feeding of feed additive mixture Mg-Increase % | after feeding of feed additive mixture Mg-Increase % | without feed additive mixture Mg-Increase % |
| Control Group | 0 | −3,2 | − 3,6 | − 2,2 |
| 40 mg Mg++(Mg Asp HCl) | 0 | +1,1 | +10,5 | +10,0 |
| 60 mg Mg++(Mg Asp HCl) | 0 | +9,6 | +24,7 | +23,7 |

The sedative effect reaches an optimum already with a dosage of 40 mg of Mg++ (Mg Asp HCl).

Magnesium glutamate chloride as well as magnesium aspartate chloride can be produced on a practical scale in accordance with the process described in German patent application No. 2 228 101, which comprises preparation of a solution of a mixture of equimolecular amounts of a magnesium salt of an aminodicarboxylic acid and magnesium chloride, and recovering the complex compound so formed in solid condition by spray-drying.

The preparations of the invention comprising the magnesium compound or mixture may be provided in various forms such as tablets, pastes or solutions comprising conventional carriers, or as an animal feed composition in the form of pellets or brickets. Preparations suitable for oral administration are preferred, but injectable solutions may also be prepared.

Similarly, a preparation of the invention may be in the form of a feed additive comprising the magnesium compound or mixture in association with conventional feed additive carrier materials.

Administration of the preparations of the invention may be effected in a single or divided doses, preferably at a daily oral dosage of from about 100 mg to about 2 g/kg animal body weight, or if by injection at a dosage of from about 10 to about 300 mg/kg animal body weight.

For the purpose of inhibiting losses of the nature encountered with animals being transported, or for the purpose of calming or sedating animals, such as may be desired before weighing or other handling operations, the animals should preferably be treated 1 to 3 days before the transport or handling is to take place. To inhibit cannibalism in pigs, a longer period of treatment can also be carried out, optionally at lower dosages.

As the following examples reflect, a drastic inhibition of cannibalism in pigs is achieved by treatment with preparations of the invention and also an inhibition of transport losses. To this is added that, for example in the liver, no physiologically unacceptable residuals are to be found. There is accordingly no reason to prevent human consumption of the livers of animals which have been treated with preparations of the invention, even if treatment may have been over an extended period.

EXAMPLE 1

Inhibition of cannibalism in pigs.

1856 pigs in the weight class of from 30 to 100 kg were fed with a feed over a period of 1½ to 5 days, on average 2 days, comprising a magnesium aspartate chloride additive preparation of the invention, at a dosage of from about 20 to 40 mg Mg++/kg on average about 30 mg Mg++/kg. All animals were in a calm state and no there were no cases of cannibalism.

EXAMPLE 2

Transport losses in pigs.

Magnesium aspartate chloride was administered to 428 slaughter pigs for 3 days at a daily dose of about 40 mg Mg++/kg animal body weight, and compared with 190 untreated control animals.

On the fourth day the animals were transported to a slaughter house. The treated animals were in a calm state, whereas the untreated animals were possessed of the usual excitement during transportation and were aggressive.

EXAMPLE 3

Weighing experiment with cattle.

Magnesium aspartate chloride was administered with a conventional feed to 1189 slaughter cattle over a period of two days at a daily dose of from about 20 to 60 mg Mg++/kg animal body weight. Whilst the treated animals could be observed to be in a state of calm during weighing, 299 untreated animals were significantly more nervous and difficult to handle.

What is claimed is:

1. A method of sedating a warm-blooded animal other than human, selected from the group consisting of horses, cattle, pigs, sheep and poultry, comprising the step of administering to such a warm-blooded animal which it is desired to sedate, a magnesium aminodicarboxylic acid chloride, or a magnesium salt of an aminodicarboxylic acid in combination with magnesium chloride, at a dosage sufficient to sedate said warm-blooded animal and said aminodicarboxylic acid in each instance being selected from the group consisting of glutamic acid and aspartic acid.

2. A method according to claim 1, in which the magnesium salt of the aminodicarboxylic acid is administered in combination with an equimolecular amount of magnesium chloride.

3. A method according to claim 1, in which the magnesium salt of the aminodicarboxylic acid is selected from magnesium diglutamate and magnesium diaspartate.

4. A method according to claim 1, in which the of administration is oral and in which the daily dosage administered is from about 100 mg to about 2 g/kg animal body weight of the magnesium aminodicarboxylic acid chloride, or magnesium salt of the aminodicarboxylic acid in combination with magnesium chloride.

5. A method according to claim 4, in which the aminodicarboxylic acid chloride, or magnesium salt of the aminodicarboxylic acid in combination with magnesium chloride, is added to an animal feed in an amount sufficient to obtain said dosage.

6. A method according to claim 1, in which the mode of administration is injection and in which the daily dosage administered is from about 10 to about 300 mg/kg animal body weight of the magnesium aminodicarboxylic acid chloride, or magnesium salt of the aminodicarboxylic acid in combination with magnesium chloride.

7. A preparation for administration to a warm-blooded animal other than human and selected from the group consisting of horses, cattle, pigs, sheep and poultry, for the purpose of sedating said warm-blooded animal, said preparation comprising an animal feed carrier material for said warm-blooded animal and a sedation-effective amount of a mixture of magnesium diglutamate and magnesium chloride, or a mixture of magnesium diaspartate and magnesium chloride, wherein said preparation supplies the sedation-effective amounts of from about 10 mg to about 2 g/kg animal body weight.

8. In an animal feed for horses, cattle, pigs, sheep or poultry, the improvement comprising mixed with said animal feed, an amount sufficient to sedate a warm-blooded animal selected from the group consisting of horses, cattle, pigs, sheep and poultry of a magnesium aminodicarboxylic acid chloride, or a magnesium salt of an aminodicarboxylic acid in combination with magnesium chloride, wherein said feed supplies the amount sufficient to sedate of from about 100 mg to about 2 g/kg animal body weight and said aminodicarboxylic acid in each instance being selected from the group consisting of glutamic acid and aspartic acid.

9. An animal feed in accordance with claim 8 in the form of pellets or brickets.

* * * * *